(12) United States Patent
Natsuhori et al.

(10) Patent No.: US 10,588,505 B2
(45) Date of Patent: Mar. 17, 2020

(54) DIAGNOSIS SUPPORT APPARATUS AND METHOD

(71) Applicant: CANON KABUSHIKI KAISHA, Tokyo (JP)

(72) Inventors: Katsutoshi Natsuhori, Tokyo (JP); Shigeaki Ono, Tokyo (JP); Yukio Sakagawa, Tokyo (JP); Hiroki Uchida, Tokyo (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 159 days.

(21) Appl. No.: 15/251,615

(22) Filed: Aug. 30, 2016

(65) Prior Publication Data

US 2016/0367130 A1    Dec. 22, 2016

Related U.S. Application Data

(63) Continuation of application No. 14/011,080, filed on Aug. 27, 2013, now Pat. No. 9,439,562.

(30) Foreign Application Priority Data

Aug. 30, 2012  (JP) .................................. 2012-190576

(51) Int. Cl.
*A61B 3/12* (2006.01)
*A61B 3/00* (2006.01)
(Continued)

(52) U.S. Cl.
CPC .......... *A61B 3/0058* (2013.01); *A61B 3/0025* (2013.01); *A61B 3/102* (2013.01);
(Continued)

(58) Field of Classification Search
CPC ... A61B 3/0058; A61B 3/0025; A61B 3/1005; A61B 3/102; A61B 3/1225; G06F 19/321; G06T 7/0012
(Continued)

(56) References Cited

U.S. PATENT DOCUMENTS 7,822,622 B2    10/2010  Kaindl et al.
8,419,186 B2 *   4/2013  Isogai .................... A61B 3/102
                                                      351/206
(Continued)

FOREIGN PATENT DOCUMENTS

CN       1650312 A     8/2005
CN     101395630 A     3/2009
(Continued)

OTHER PUBLICATIONS

Japanese office action issued in corresponding application No. 2013178215 dated Jun. 6, 2017.
(Continued)

*Primary Examiner* — James R Greece
(74) *Attorney, Agent, or Firm* — Carter, DeLuca & Farrell LLP

(57) ABSTRACT

A diagnosis support apparatus comprises an acquiring unit that acquires a plurality of examination data items having different examination dates, a setting unit that sets an extraction condition for examination data items, an extracting unit that extracts, from the plurality of acquired examination data items, examination data items corresponding to the set extraction condition, and a displaying unit that arranges and displays the extracted examination data items, wherein the setting unit sets the extraction condition based on an interval between examination dates of examination data items.

44 Claims, 10 Drawing Sheets

(51) Int. Cl.
*A61B 3/10* (2006.01)
*G06F 19/00* (2018.01)
*G06T 7/00* (2017.01)

(52) U.S. Cl.
CPC .......... *A61B 3/1005* (2013.01); *A61B 3/1225* (2013.01); *G06F 19/321* (2013.01); *G06T 7/0012* (2013.01); *G06T 2207/30041* (2013.01)

(58) Field of Classification Search
USPC ........................................ 351/205, 206, 246
See application file for complete search history.

(56) References Cited

U.S. PATENT DOCUMENTS

| | | | |
|---|---|---|---|
| 8,967,804 B2 | 3/2015 | Ono | |
| 9,125,561 B2 | 9/2015 | Ono et al. | |
| 2007/0222946 A1* | 9/2007 | Fukuma ................. | A61B 3/102 351/206 |
| 2007/0230761 A1 | 10/2007 | Gundel et al. | |
| 2008/0100612 A1 | 5/2008 | Dastmalchi et al. | |
| 2010/0179824 A1 | 7/2010 | Fujimoto et al. | |
| 2011/0129133 A1 | 6/2011 | Ramos et al. | |
| 2013/0188141 A1 | 7/2013 | Nakahara et al. | |
| 2014/0063447 A1 | 3/2014 | Piotrowski et al. | |

FOREIGN PATENT DOCUMENTS

| | | |
|---|---|---|
| CN | 102473204 A | 5/2012 |
| CN | 102834839 A | 12/2012 |
| EP | 1176537 A | 1/2002 |
| EP | 1990765 A | 11/2008 |
| JP | H10-192242 A | 7/1998 |
| JP | H11-244245 A | 9/1999 |
| JP | 2000-300518 A | 10/2000 |
| JP | 2003-19118 A | 1/2003 |
| JP | 2007-287027 A | 11/2007 |
| JP | 2008-029732 A | 2/2008 |
| JP | 2008-234272 A | 10/2008 |
| JP | 2009-104278 A | 5/2009 |
| JP | 2010-0246904 A | 11/2010 |
| JP | 2011-083555 A | 4/2011 |
| JP | 2012-071113 A | 4/2012 |
| WO | 2011/122401 A | 10/2011 |

OTHER PUBLICATIONS

European Search Report issued in corresponding European application No. 13182274.4 dated Dec. 5, 2013.

Chinese Office Action issued in corresponding application No. 201310389489.1 dated Jan. 23, 2015.

Korean Office Action issued in corresponding application No. 10-2013-0100139 dated May 18, 2015.

Japanese Office Action dated Dec. 18, 2018 in corresponding Japanese Patent Application No. 2018-035447, with English translation.

Notification of Fourth Office Action issued by the China National Intellectual Property Administration dated Dec. 5, 2018 in corresponding Chinese Patent Application No. 201510708157.4 with English translation.

Notice of Reasons for Refusal issued by the Japanese Patent Office dated Jul. 9, 2019 in corresponding Japanese Patent Application No. 2018-035447, with English translation.

* cited by examiner

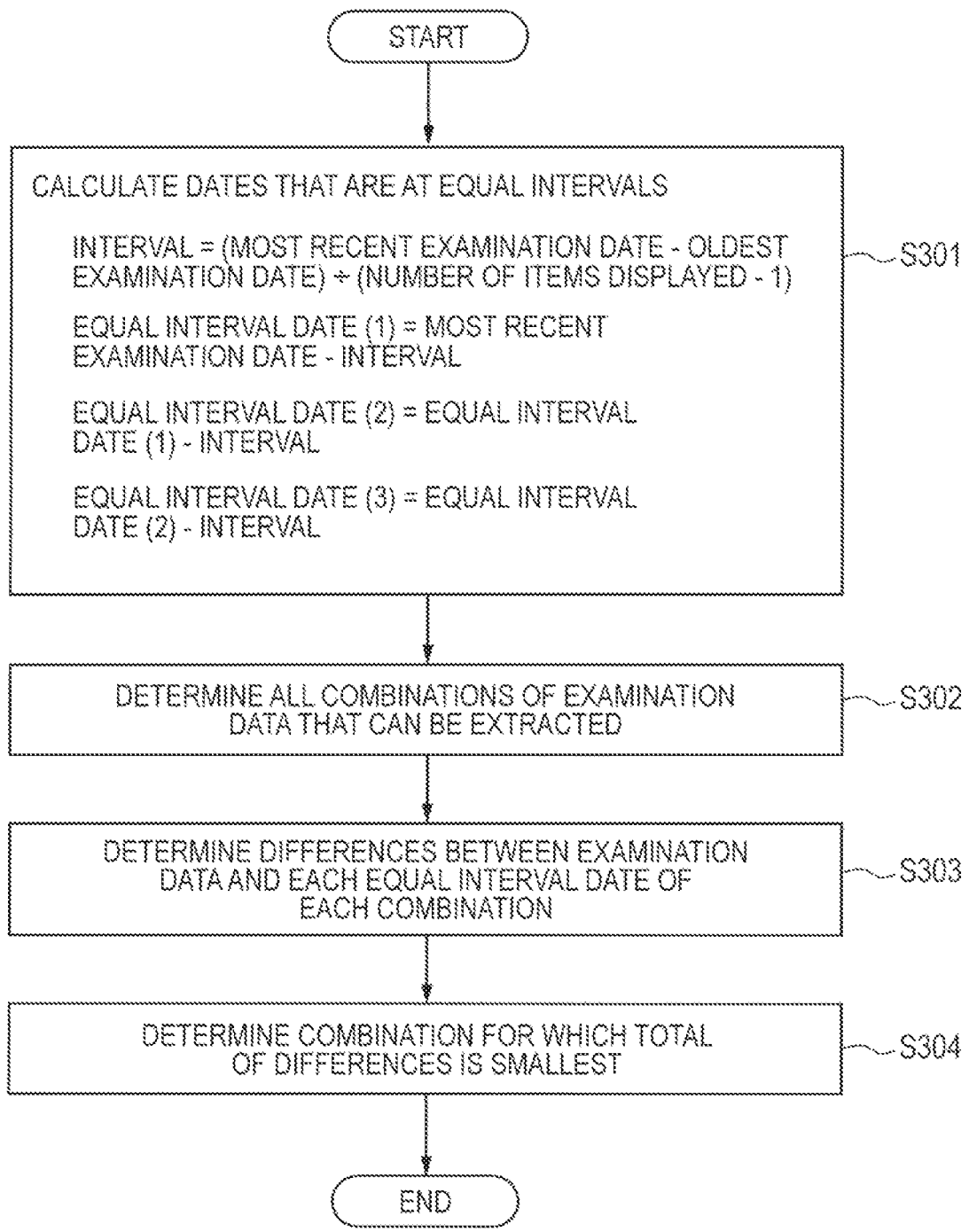

FIG. 4A

| No | EXAMINATION DATE | NUMBER OF DAYS DIFFERENCE |
|---|---|---|
| 6 | 2012/6/1 | 0 |
| 5 | 2012/3/2 | 91 |
| 4 | 2011/12/8 | 176 |
| 3 | 2011/9/5 | 270 |
| 2 | 2011/5/23 | 375 |
| 1 | 2011/2/15 | 472 |

FIG. 4B

COMBINATION (1)

| No | EXAMINATION DATE | EQUAL INTERVAL DATE | NUMBER OF DAYS DIFFERENCE |
|---|---|---|---|
| 5 | 2012/3/2 | 2012/2/4 | 27 |
| 4 | 2011/12/8 | 2011/10/9 | 60 |
| 3 | 2011/9/5 | 2011/6/13 | 84 |
| | | TOTAL | 171 |

FIG. 4C

COMBINATION (2)

| No | EXAMINATION DATE | EQUAL INTERVAL DATE | NUMBER OF DAYS DIFFERENCE |
|---|---|---|---|
| 5 | 2012/3/2 | 2012/2/4 | 27 |
| 4 | 2011/12/8 | 2011/10/9 | 60 |
| 2 | 2011/5/23 | 2011/6/13 | 21 |
| | | TOTAL | 108 |

FIG. 4D

COMBINATION (3)

| No | EXAMINATION DATE | EQUAL INTERVAL DATE | NUMBER OF DAYS DIFFERENCE |
|---|---|---|---|
| 5 | 2012/3/2 | 2012/2/4 | 27 |
| 3 | 2011/9/5 | 2011/10/9 | 34 |
| 2 | 2011/5/23 | 2011/6/13 | 21 |
| | | TOTAL | 82 |

FIG. 4E

COMBINATION (4)

| No | EXAMINATION DATE | EQUAL INTERVAL DATE | NUMBER OF DAYS DIFFERENCE |
|---|---|---|---|
| 4 | 2011/12/8 | 2012/2/4 | 58 |
| 3 | 2011/9/5 | 2011/10/9 | 34 |
| 2 | 2011/5/23 | 2011/6/13 | 21 |
| | | TOTAL | 113 |

FIG. 4F

| No | EXAMINATION DATE | INDIVIDUAL INTERVAL DATE | NUMBER OF DAYS DIFFERENCE |
|---|---|---|---|
| 5 | 2012/3/2 | 2012/3/2 | 0 |
| 4 | 2011/12/8 | 2011/12/2 | 6 |
| 2 | 2011/5/23 | 2011/6/2 | 10 |
| | | TOTAL | 16 |

FIG. 4G

| No | EXAMINATION DATE | INDIVIDUAL INTERVAL DATE | NUMBER OF DAYS DIFFERENCE |
|---|---|---|---|
| 5 | 2012/3/2 | 2012/5/2 | 61 |
| 4 | 2011/12/8 | 2012/3/2 | 85 |
| 3 | 2011/9/5 | 2011/12/2 | 88 |
| | | TOTAL | 234 |

FIG. 4H

| No | EXAMINATION DATE | INDIVIDUAL INTERVAL DATE | NUMBER OF DAYS DIFFERENCE |
|---|---|---|---|
| — | No Data | 2012/5/2 | — |
| 5 | 2012/3/2 | 2012/3/2 | 0 |
| 4 | 2011/2/8 | 2011/12/2 | 6 |
| | | TOTAL | 6 |

DIAGNOSIS SUPPORT APPARATUS AND METHOD

CROSS REFERENCE TO RELATED APPLICATIONS

This application is a continuation of U.S. patent application Ser. No. 14/011,080 filed on Aug. 27, 2013, which claims the benefit of and priority to Japanese Patent Application No. 2012-190576, filed on Aug. 30, 2012, each of which are hereby incorporated by reference herein in their entirety.

BACKGROUND OF THE INVENTION

Field of the Invention

The present invention relates to a diagnosis support apparatus and method, and more particularly to technology for efficiently performing ophthalmic image diagnosis.

Description of the Related Art

In order to perform a follow-up observation with respect to the symptoms of a patient, examination data such as images relating to each patient is stored, and retrieval of examination data that is required for observation is performed on the basis of photographing conditions. Technology is already available that displays retrieved examination data in reverse chronological order from the most recent examination data (Japanese Patent Application Laid-Open No. 2003-19118). Further, when a desired examination data item is selected as a comparison source from a displayed examination data list, data that relates to the selected data, for example, data from the immediately preceding examination or data for the opposite eye, is automatically selected as the data of the comparison target, and is displayed in parallel with the comparison source. Technology is also available that allows a user to manually select a plurality of data items to thereby display the selected data items in chronological order (Japanese Patent Application Laid-Open No. 2000-300518). In recent years, it has become possible to quantify the retinal layer thickness or nerve fiber layer thickness and the like by analyzing a fundus tomogram that was imaged by OCT (optical coherence tomography), and thus follow-up observation for diagnosis is becoming increasingly important.

SUMMARY OF THE INVENTION

In a case where a period of treatment or the like is a long period and a large number of examinations are performed during that period and a large number of examination data items exist, if only data from some of the most recent examinations is displayed and observed, there is the problem that it is not possible to adequately ascertain the progress situation over a long period. Further, in a case where a user desires to view several items of examination data that were obtained at certain time intervals in order to ascertain the progress situation over a long period, it is necessary for the user to select examination data items from a large amount of examination data while manually checking the examination dates of the data items, and there is the problem that these are time- and labor-consuming operations.

To solve the above described problems, the present invention provides a diagnosis support apparatus that includes: an acquiring unit that acquires a plurality of examination data items having different examination dates; a setting unit that sets an extraction condition for examination data items; an extracting unit that extracts, from the plurality of acquired examination data items, examination data items corresponding to the set extraction condition; and a displaying unit that arranges and displays the extracted examination data items, wherein the setting unit is configured to set the extraction condition based on an interval between examination dates of examination data items.

A progress situation over a long period can thus be easily ascertained.

Further features of the present invention will become apparent from the following description of exemplary embodiments with reference to the attached drawings.

BRIEF DESCRIPTION OF THE DRAWINGS

FIG. 3 is a flowchart illustrating processing for extracting data.

FIGS. 4A, 4B, 4C, 4D, 4E, 4F, 4G and 4H are views illustrating combinations of data items that relate to data extraction.

FIG. 5 is a view illustrating a patient selection screen.

FIG. 7 is a view illustrating another example of a report screen.

FIGS. 8A, 8B, 8C, and 8D are views illustrating a "Select" screen.

FIG. 9 is a view illustrating a further example of a report screen.

DESCRIPTION OF THE EMBODIMENTS

Figure 1:
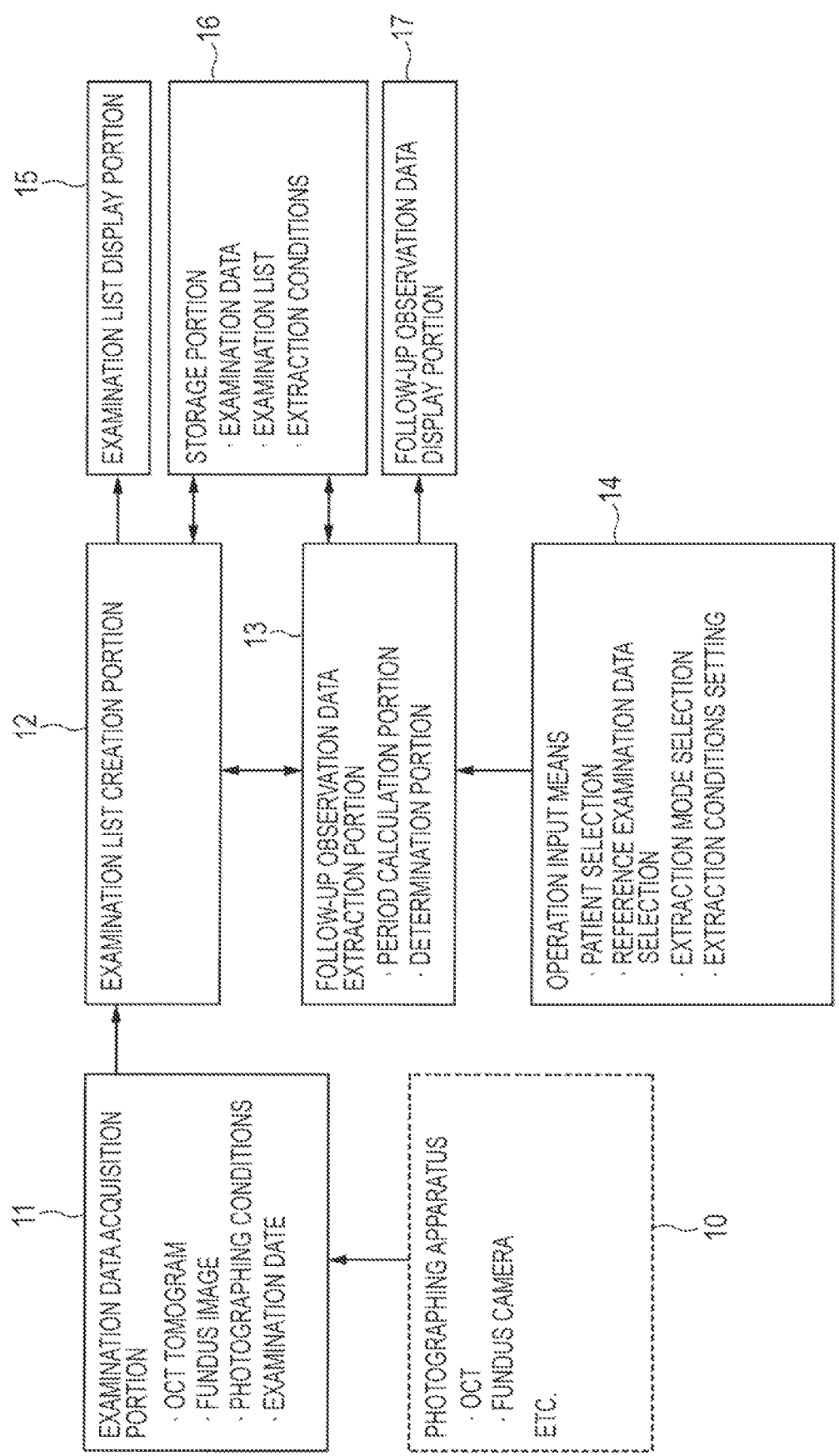
FIG. 1 is a view illustrating the configuration of a diagnosis support apparatus according to an embodiment of the present invention.

Exemplary embodiments for implementing the present invention are described hereunder with reference to the drawings. FIG. 1 illustrates the configuration of a diagnosis support apparatus according to the embodiments. The present diagnosis support apparatus includes an examination data acquisition portion 11, an examination list creation portion 12, a follow-up observation data extraction portion 13, operation input means 14, an examination list display portion 15, a storage portion 16, and a follow-up observation data display portion 17.

Hereunder, a configuration is described in which the diagnosis support apparatus according to the embodiments and a photographing apparatus 10 that is an external apparatus are combined. Although an OCT (optical coherence tomography) photographing apparatus that is one kind of ophthalmic photographing apparatus may be mentioned as an example of the photographing apparatus 10, the present diagnosis support apparatus is not limited to a configuration in which the diagnosis support apparatus is combined with an ophthalmic photographing apparatus, and can also be applied to a combination with a photographing apparatus of another medical department.

In FIG. 1, a plurality of images that were imaged by the photographing apparatus 10 are acquired by the diagnosis support apparatus by means of the examination data acquisition portion 11. Photographing conditions such as the examination date and photographing mode are acquired together with the images. An examination list that is linked to the patient is created by the examination list creation portion 12 based on the acquired examination data. The examination list is displayed on the examination list display portion 15. The examination data and examination list are stored in the storage portion 16. Examination data is acquired each time an examination of the patient is performed, and is stored as a large number of time-series data items over a long period.

Embodiment 1

Figure 2:
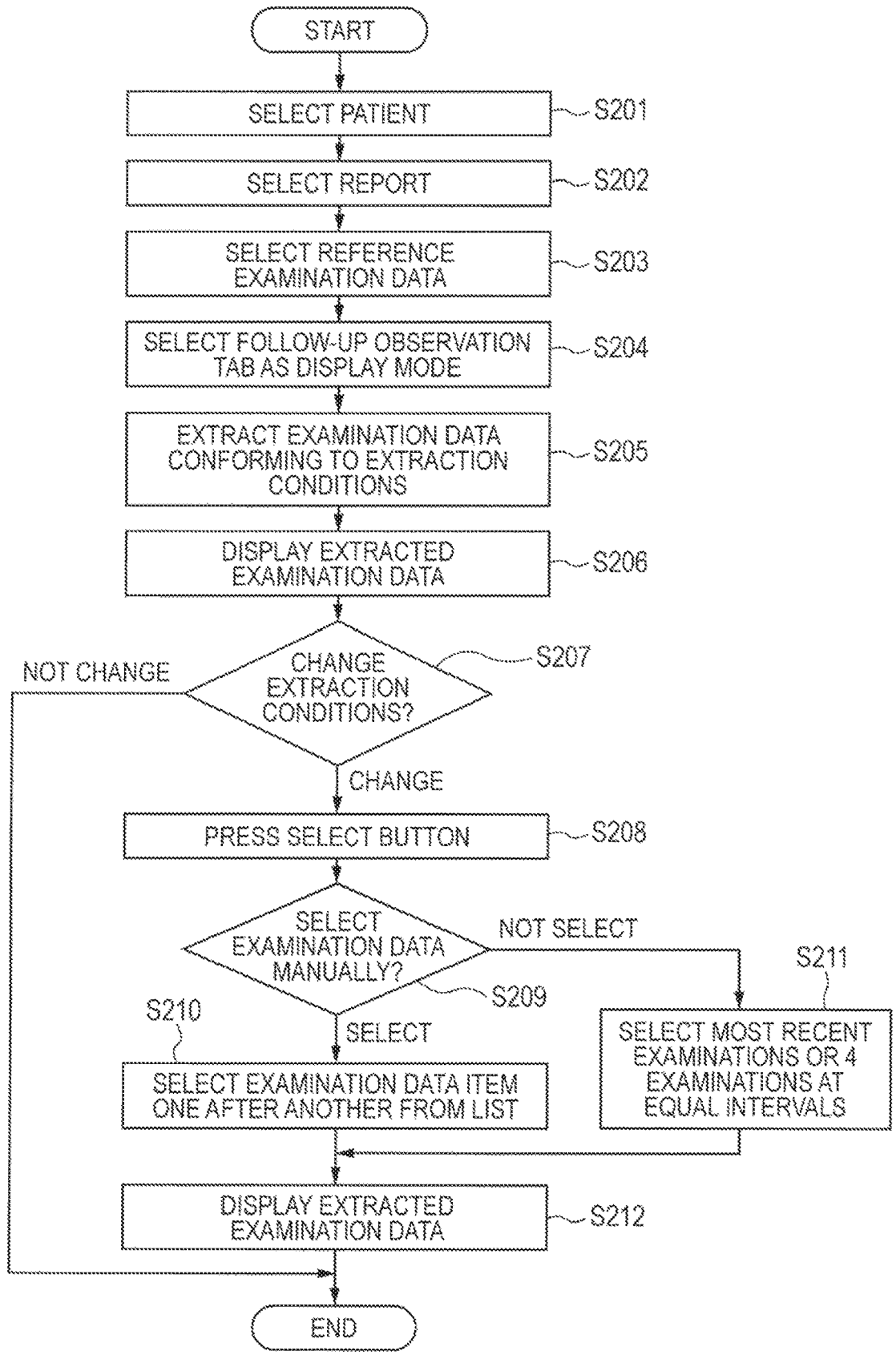
FIG. 2 is a flowchart illustrating processing performed by the diagnosis support apparatus according to an embodiment of the present invention.
Figure 5:
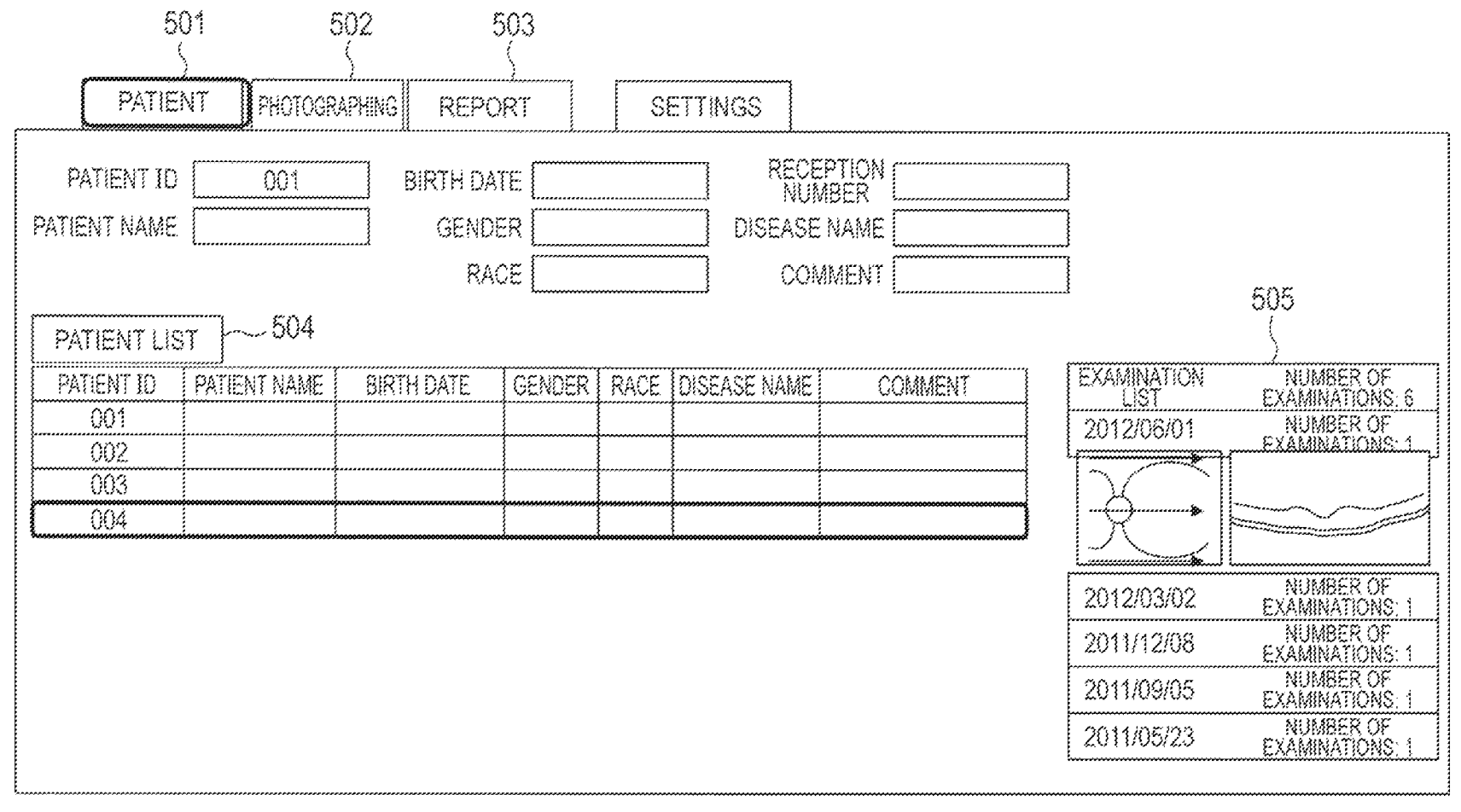

FIG. 2 illustrates a flow of processing when performing a follow-up observation. First, in step S201, the patient is selected. FIG. 5 illustrates a screen for performing patient selection. When the user selects a tab 501 that is a "patient" tab on this screen, the user can newly register a patient, edit existing information, or select a patient. If the user inputs a patient ID or patient name using the operation input means 14, a patient list 504 that shows the retrieved patients is displayed. In the present example, a case is described in which results obtained by searching with a patient ID are displayed and the user selects a patient with a patient ID 004 from the results. The examination data of the patient that was selected is read from the storage portion 16. The examination list 505 for the selected patient is created by the examination list creation portion 12, and is displayed in thumbnail format in a display area on the right side of the patient screen by the examination list display portion 15.

In FIG. 5, when the user selects a tab 502 that is a "photographing" tab, the screen transitions to a screen for photographing with the photographing apparatus 10. On the photographing screen, the user performs operations to carry out an examination in a desired photographing mode. As described above, the images obtained by photographing are acquired by the examination data acquisition portion 11, the relevant information is added to the examination list by the examination list creation portion 12, and the examination data and examination list are stored in the storage portion 16. A description of the photographing screen is omitted herein.

Figure 6:
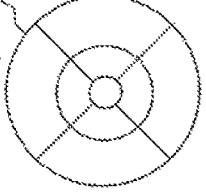
FIG. 6 is a view illustrating an example of a report screen.

In step S202, to view information relating to the follow-up observation of the patient identified by the ID 004, the user selects a "report" tab 503 shown in FIG. 5 to thereby transition to a report screen. FIG. 6 illustrates an example of the report screen with the "report" tab 601 selected at the top. In FIG. 6, patient information is displayed in an upper part 602 of the screen and an examination list is displayed on a left side 603 of the screen. Two kinds of lists are available for display, namely, a date order list and a mode order list, and the user can select the desired kind of list by selecting the corresponding tab. Further, for each photographing mode, information for the left eye and for the right eye is classified separately and made into a list. FIG. 6 illustrates a case where a mode order list 605 is selected. In FIG. 6, a list of examination data that was imaged in a photographing mode called "Macula 3D" is displayed in reverse chronological order separately for the left eye and right eye. In the example shown in FIG. 6, data for the left eye is selected, and information showing that the number of examinations is six is displayed, and a thumbnail image of each examination is also displayed in list format. In this example, it is found that the date of the most recent examination of the left eye in the Macula 3D photographing mode was 2012 Jun. 1 (i.e. 1 Jun. 2012).

A right side 604 from the center of the report screen in FIG. 6 is a display area that displays examination results and analysis results. Six display modes are available in the display area 604, namely, "Single", "Both Eyes", "Comparison", "Progression", "General", and "3D" display modes. It is assumed that settings have been made so that, immediately after transitioning to the report screen, examination data 2012 Jun. 1 for the most recent examination on 2012 Jun. 1 is selected and the display mode is the "Single" mode 606. The "Single" mode is a mode that displays data in selected examination units. In the "Single" mode, an analysis map 607, a main scanning tomogram 608, and a sub-scanning tomogram 609 are displayed in the display area 604. When the user wants to view other examination data, the user can change the selection in the mode order list 605 using the operation input means 14 to thereby switch the examination data to be displayed and view the relevant examination data.

In step S203, reference examination data is selected. The term "reference examination data" refers to the most recent examination data among the examinations for which the user desires to perform the follow-up observation, and means that data acquired in examinations performed prior to the examination in which the reference examination data was acquired is taken as the display target for the follow-up observation. In FIG. 6, a case is illustrated in which, when the user brings a mouse cursor (illustrated as an arrow) over the thumbnail image for examination data for the left eye acquired on 2012 Jun. 1 and clicks on the thumbnail image, the examination data for 2012 Jun. 1 is selected as the reference examination data.

Figure 7:
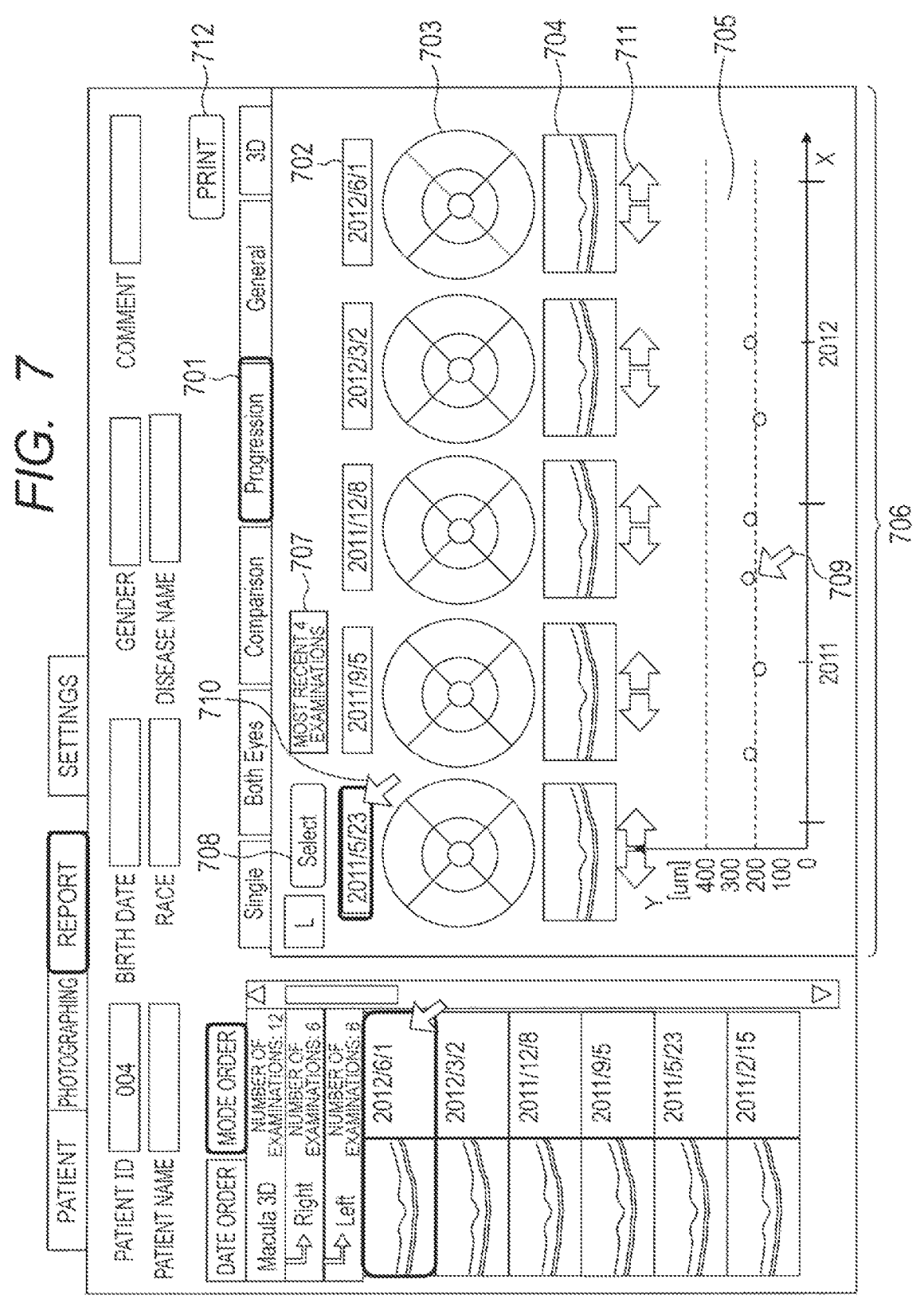

In step S204, follow-up observation is selected as the display mode. By selecting a "Progression" tab 701 on the report screen, the user causes the display mode to transition from "Single" to "Progression" (FIG. 7). The "Progression" mode is a display mode for a follow-up observation.

In step S205, examination data that conforms to an extraction condition is extracted. The follow-up observation data extraction portion 13 extracts examination data conforming to a predetermined extraction condition from among examination data that is an extraction target in the examination list. It is assumed that there are two extraction conditions, namely, a condition that extracts the most recent four examinations and a condition that extracts four examinations at equal intervals. The term "extracts the most recent four examinations" 707 refers to extracting examination data for the nearest four examinations to the reference examination data. When this condition is selected, examination data for a total of five examinations that include the reference examination data and the examination data for the four examinations that are nearest thereto are arranged and displayed. The term "extracts four examinations at equal intervals" refers to extracting examination data so that the intervals between the dates at which the examination data items were acquired are approximately equal by dividing a period between the examination date of the reference examination data and the examination date of the oldest examination data into four equal parts, and extracting examination data items obtained on dates that are nearest the dates at which the aforementioned period is divided into four equal parts. When this condition is selected, data for a total of five examinations is in fact displayed (four plus the most recent), namely, the two examinations in which the reference examination data and the oldest examination data were obtained, and the three examinations on the dates that are nearest the respective dates at which the aforementioned period is divided into four equal parts. Note that although equal intervals are used according to the present embodiment, as described later, other predetermined intervals can also be used.

It is assumed that the most recent four examinations condition is set as the default extraction condition when transitioning to the "Progression" screen. In this case, the examination data obtained on 2012 Jun. 1 is taken as the first data, and data for the most recent four examinations prior to that date is extracted. The default extraction condition can be changed using the settings. A configuration may also be adopted so as to store the condition that was used previously as an extraction condition, and to continue to use that condition.

Figure 10:
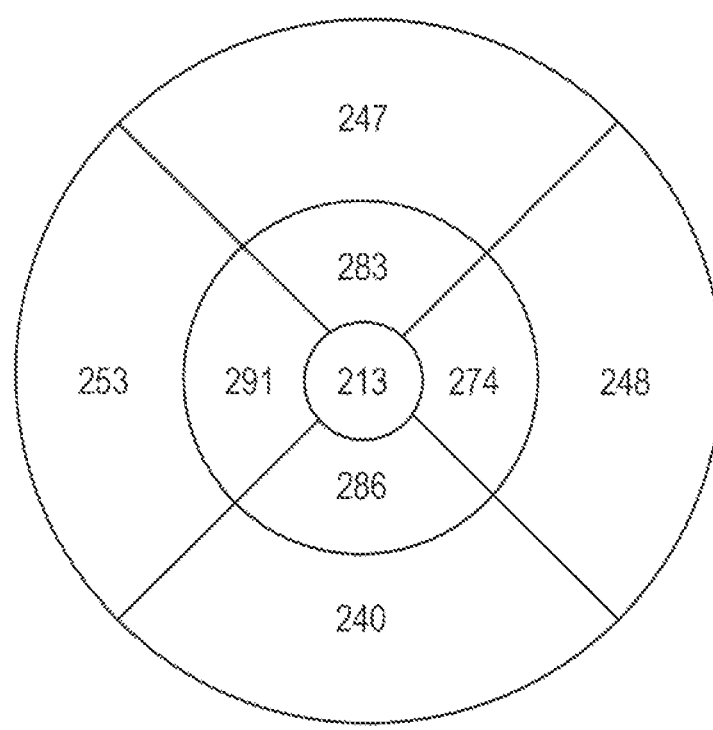
FIG. 10 is a view illustrating a display that shows retinal thicknesses in sectors.

In step S206, the extracted examination data is displayed. The follow-up observation data display portion 17 displays the extracted five examination data items in a display area 706 shown in FIG. 7. The five examination data items are arranged in chronological order and displayed from the left to the right side, with the reference examination data acquired on 2012 Jun. 1 displayed at the right end. The number of examinations that can be displayed is five, and since the most recent four examinations is set as the extraction condition, the data acquired on 2011 Feb. 15 is not extracted and is not displayed. In the display area 706, a date 702, an analysis map 703, a tomogram 704, and a graph 705 are displayed in parallel for each examination data item. For example, as shown in FIG. 10, a map in which retinal thicknesses are displayed in sectors is displayed as the analysis map 703. The graph 705 is a graph that plots values at the center sector in the retinal thickness maps. The X-axis represents the date, and the Y-axis represents the thickness [μm] of the retina. A configuration is adopted that enables the user to previously select and set what to display in the respective display areas of the analysis map, the tomogram, and the graph.

Regarding the display method, although a condition that the number of examinations that can be displayed is five is described as a condition according to the present example, the number of examinations that can be displayed is not limited and may be decided according to the display size, and may be for example 10 examinations. Further, even when the number of examinations that can be displayed simultaneously is five, a configuration may be adopted in which a slide bar is provided so as to display examination data while forwarding to a subsequent examination or returning to a previous examination. A configuration may also be adopted that displays examination data in two tiers that are above and below each other, with five examination data items being displayed on the upper tier and the lower tier, respectively. Furthermore, a configuration may be adopted that displays data for the left and right eyes, in which data for the left eye is displayed on the upper tier and data for the right eye is displayed on the lower tier. Note that the current extraction condition is displayed in an extraction condition display portion 707.

In step S207, the user views the five examination data items that are displayed and decides whether or not to change the extraction condition. If the user decides to change the extraction condition, the process advances to step S208.

Figures 8A, 8B, 8C, 8D:
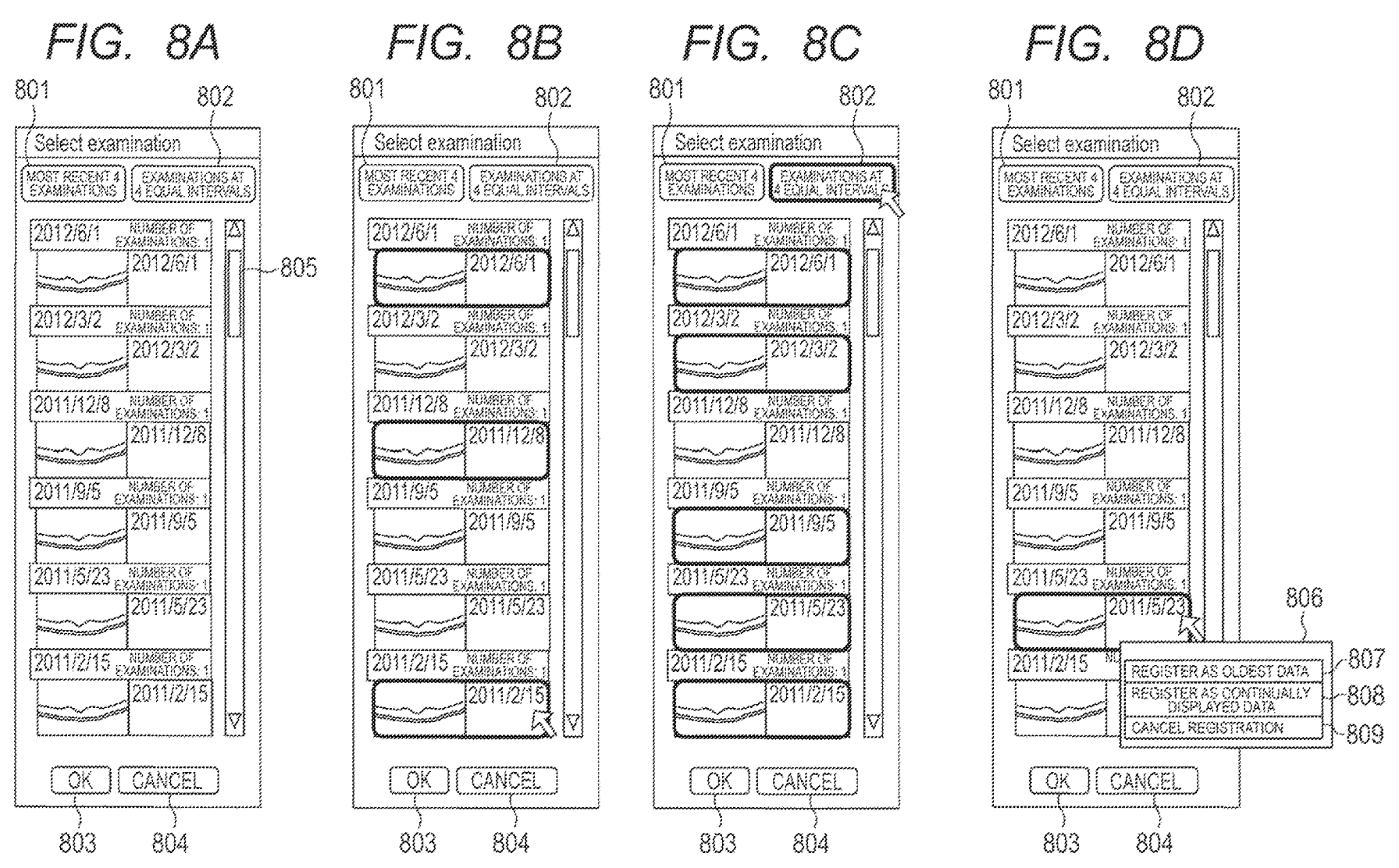

In step S208, the user presses a "Select" button 708. Thereupon, a "Select" screen as shown in FIG. 8A is displayed. On the "Select" screen, only examination data that is the target of the follow-up observation is displayed as a list. In the examination list that is displayed on the "Select" screen, data is displayed that has been narrowed down from among the entire examination data to only the examination data that satisfies the condition of being acquired in the same photographing mode as the reference examination data and of relating to the same left or right eye. This condition for narrowing down the examination data that is to be displayed is a condition for taking only examination data that is useful from the viewpoint of the follow-up observation as a target. The user can check all the examination data that is an extraction target by moving a slide bar 805. Further, to allow the user to select the extraction condition, a button 801 that can select the condition "most recent four examinations" and a button 802 that can select the condition "four examinations at equal intervals" are disposed on the "Select" screen.

In step S209, the user decides whether or not to manually select examination data. If the user decides to manually select examination data, the process advances to step S210. If the user decides not to manually select examination data, the process advances to step S211.

In step S210, the user manually selects examination data items one by one from the list. The user can switch between selecting and not selecting examination data items in the examination list in the "Select" screen by using the mouse to click on the thumbnail of the respective examination data items. As shown in FIG. 8A, in a state in which there is no selected examination data item, the user selects the examination data items that the user wishes to view by clicking on the relevant thumbnails one by one. If the user wants to cancel selection of an examination data item that the user selected, the user can cancel the selection by clicking on the thumbnail again. FIG. 8B shows an example in which the user selected three examination data items, namely data for the examinations on 2012 Jun. 1, 2011 Dec. 8, and 2011 Feb. 15.

In addition to the above described method, the following methods are also conceivable as methods of performing a manual selection. First, a configuration may be adopted that allows a user to perform selection and deselection operations by clicking on points corresponding to the respective examination data items on the graph 705 on the report screen shown in FIG. 7 using a mouse cursor 709. Further, a configuration may be adopted that allows a user to click on and select the date 702 of one examination data item that the user wishes to change on the aforementioned report screen using a mouse cursor 710. In FIG. 7, a state is illustrated in which the user selected the date of the examination data of 2011 May 23. In the selected state, the user can advance to a next examination or go back to a previous examination by moving a wheel of the mouse forward or rearward. A configuration may also be adopted in which, instead of using the wheel of a mouse, an unshown drop-down menu is displayed, and 2011 Feb. 15 as candidate data to which a change can be made is displayed and which can be selected. Further, as shown in FIG. 7, buttons 711 that allow the user to change the displayed examination data to the next/previous examination data may be provided. The buttons 711 for displaying the next/previous examination data are enabled only when there is non-displayed examination data that was obtained before or after the relevant examination data.

In step S211, the user selects either "most recent four examinations" or "four examinations at equal intervals". These extraction conditions represent an example of the extraction conditions, and a configuration may be adopted that enables selection of various other conditions. If the user wishes to view four examinations at equal intervals, as shown in FIG. 8C, the user can easily change the condition by pressing the button 802. After the button 802 is pressed, the follow-up observation data extraction portion 13 performs extraction again in accordance with the changed extraction condition (an extraction algorithm is described later). The color of the thumbnails of the extracted examination data items changes, and the user can recognize which examination data items were extracted. As shown in FIG.

8C, thumbnails surrounded by a thick line indicate extracted examination data items, and it is possible to visually distinguish that the examination data of 2011 Dec. 8 was not extracted. Thereafter, the user can change the condition to the most recent four examinations again by pressing the button 801.

In step S212, the extracted examination data is displayed. The user selects an extraction condition on the "Select" screen, and presses an "OK" button 803 when extraction is completed. The "Select" screen closes and the extracted data is displayed on the follow-up observation data display portion 17. If the user wants to cancel the selection of the extraction condition, the user may press a "cancel" button 804. The user can output the extracted examination data as a report in a predetermined format by pressing a "print" button 712.

Next, an extraction algorithm in a case where the user selected "four examinations at equal intervals" in step S211 is described using FIG. 3 and FIG. 4A to FIG. 4H. FIG. 3 is a view that illustrates an extraction process, and FIG. 4A to FIG. 4H are views that illustrate examination list combinations. It is assumed that, with respect to the extraction conditions, a range that is the target of extraction is all examination data prior to the reference examination data, the intervals are equal intervals, and the number of displayed examinations is five.

FIG. 4A illustrates an example of an examination list, which shows that the data of 2011 Feb. 15 is the oldest examination data, the data of 2012 Jun. 1 is the most recent examination data, and there is a total of six data items. With respect to the condition that the number of examination data items that can be displayed on the follow-up observation screen is five, since the oldest data No. 1 and the most recent data No. 6 are necessarily displayed, the remaining three data items to be displayed are extracted.

In step S301, dates that are at equal intervals (equal interval dates) are determined by calculation. The total period is the number of days' difference between the most recent data No. 6 and the oldest data No. 1, which is 472 days. The total period of 472 days is divided by 4, which is the number obtained by subtracting 1 from 5 that is the number of displayed items (i.e. to make 4 intervals), to thereby determine that the interval is 118 days. When the date that is prior to 2012 Jun. 1 that is the date of the most recent data No. 6 by the number of interval days 118 is calculated, it is found that equal interval date (1) is 2012 Feb. 4. When the date that is prior to 2012 Feb. 4 that is the equal interval date (1) by the number of interval days 118 is calculated, it is found that equal interval date (2) is 2011 Oct. 9. When the date that is prior to 2011 Oct. 9 that is the equal interval date (2) by the number of interval days 118 is calculated, it is found that equal interval date (3) is 2011 Jun. 13.

In step S302, all combinations of the examination data that can be extracted are determined. In the examination data shown in FIG. 4A, the four data items with data Nos. 2 to 5 are the targets for combination. Four combinations are obtained by extracting three data items from the aforementioned four data items. The four combinations are shown in FIGS. 4B to 4E.

In step S303, differences between the dates of the examination data and the equal interval dates of each combination are determined. The difference is an absolute value, and a symbol is not attached to indicate whether the difference relates to the relevant examination date being before or after the equal interval date. Taking combination (1) shown in FIG. 4B as an example, when the number of days difference between 2012 Mar. 2 that is the date of data No. 5 and 2012 Feb. 4 that is equal interval date (1) is determined, it is found that the number of days difference is 27 days. Likewise, the number of days difference between 2011 Dec. 8 that is the date of data No. 4 and 2011 Oct. 9 that is equal interval date (2) is 60 days, and the number of days difference between 2011 Sep. 5 that is the date of data No. 3 and 2011 Jun. 13 that is equal interval date (3) is 84 days. Further, when the total number of days difference of the respective data items is calculated, it is found that the total number of days difference is 171 days. Although differences are calculated as a simple sum according to the present example, the calculation method is not limited thereto, and a method may also be used that obtains a minimum sum of squares of the differences.

In step S304, the combination with the smallest total number of days difference is determined. The total value for the number of days difference of the respective combinations is 171 days for combination (1), 108 for combination (2), 82 days for combination (3), and 113 days for combination (4). Hence, combination (3) is the combination with the smallest total. Therefore, combination (3) is extracted as the examination data of examinations at equal intervals.

Embodiment 2

Although in Embodiment 1 the intervals between dates of examination data were made equal intervals, according to Embodiment 2 the intervals are not made equal, but are set individually. Hereunder, a case is described in which an initial interval is set as a fixed value of three months (91 days), the next interval is set as a fixed value of six months (182 days), and the subsequent interval is set as a fixed value of 12 months (365 days), i.e. the intervals are set to a ratio (1:2:4) with respect to three months. Note that the entire processing flow is the same as in Embodiment 1 with the exception that, in step S211 in FIG. 2, examinations at equal intervals are replaced with individual interval examinations. Therefore, a description of the processing flow is omitted here.

In step S301 in FIG. 3, individual interval dates (1), (2), and (3) are calculated instead of the equal interval dates (1), (2), and (3). With respect to the examination data shown in FIG. 4A, by calculating a date for which the number of interval days prior to the date 2012 Jun. 1 of the most recent data No. 6 is 91 days, it is found that individual interval date (1) is 2012 Mar. 2. Likewise, by calculating dates that are 182 days and 365 days before the date 2012 Jun. 1 of the most recent data No. 6, it is found that individual interval date (2) is 2011 Dec. 2 and individual interval date (3) is 2011 Jun. 2. Next, in step S302, all combinations of the examination data that can be extracted are determined. Thereafter, in step S303, differences between the dates of the examination data and the individual interval dates of the respective combinations of examination dates shown in FIGS. 4B to 4E are determined. In step S304, the combination with the smallest total difference is determined. In this case, the combination shown in FIG. 4F has the smallest total difference. This combination (3) is extracted as examination data.

Embodiment 3

In Embodiment 1 intervals between dates of examination data were made equal intervals, and in Embodiment 2 the intervals were not made equal, but were set individually. According to Embodiment 3, processing is described for a case where there is no examination data that was obtained on a date near to an equal interval date or an individual interval date (the number of days difference is large). Note that since the remaining processing flow is the same as in Embodiments 1 and 2, a description thereof is omitted here.

Various cases are conceivable with regard to combinations of examination dates of examination data, and depending on the interval setting, in some cases there is no examination data that is near to a certain interval date. That is, the number of days' difference with respect to an interval date is large in some cases. As one example, a case will now be described in which, with respect to the examination data shown in FIG. 4A, intervals are set individually so that the first interval is one month (30 days), the next interval is three months (91) days, and the next interval is six months (182) days. In this case, when dates are calculated that are prior to 2012 Jun. 1 that is the date of the most recent data No. 6 by 30 days, 91 days, and 182 days that are the aforementioned numbers of interval days, it is found that individual interval date (1) is 2012 May 2, individual interval date (2) is 2012 Mar. 2, and individual interval date (3) is 2011 Dec. 2. According to the aforementioned algorithm, it is found the total number of days' difference is smallest in a combination shown in FIG. 4G.

However, since there is no examination data that is close to individual interval date (1) 2012 May 2, the examination performed on 2012 Mar. 2 is assigned to the interval date (1). The data of the examination performed on 2012 Mar. 2 is the data of the nearest examination to individual interval date (2) 2012 Mar. 2. Likewise, although the examination performed on 2011 Dec. 8 is assigned to the individual interval date (2) 2012 Mar. 2, the data for the examination performed on 2011 Dec. 8 is the data of the nearest examination to individual interval date (3) 2011 Dec. 2. Thus, when appropriate data does not exist, in some cases the interval dates and the actual examination dates that are displayed are separated by a large number of days.

One method for rectifying this problem will now be described. According to this method, in a case where appropriate data does not exist for a certain interval date, the relevant interval date is displayed as an interval date for which there is no corresponding data, and the interval date is question is excluded from data extraction conditions. As one example of a determination regarding whether data does not exist, it is determined whether or not there is examination data that was obtained within a predetermined range before and after a certain interval date. It is assumed that the range is as far as dates that are midway between the certain interval date and the neighboring interval dates. The range of individual interval date (1) 2012 May 2 is from 2012 May 17 that is midway between individual interval date (1) 2012 May 2 and the most recent examination date 2012 Jun. 1, to 2012 Apr. 1 that is midway between individual interval date (1) 2012 May 2 and individual interval date (2) 2012 Mar. 2.

Figure 9:
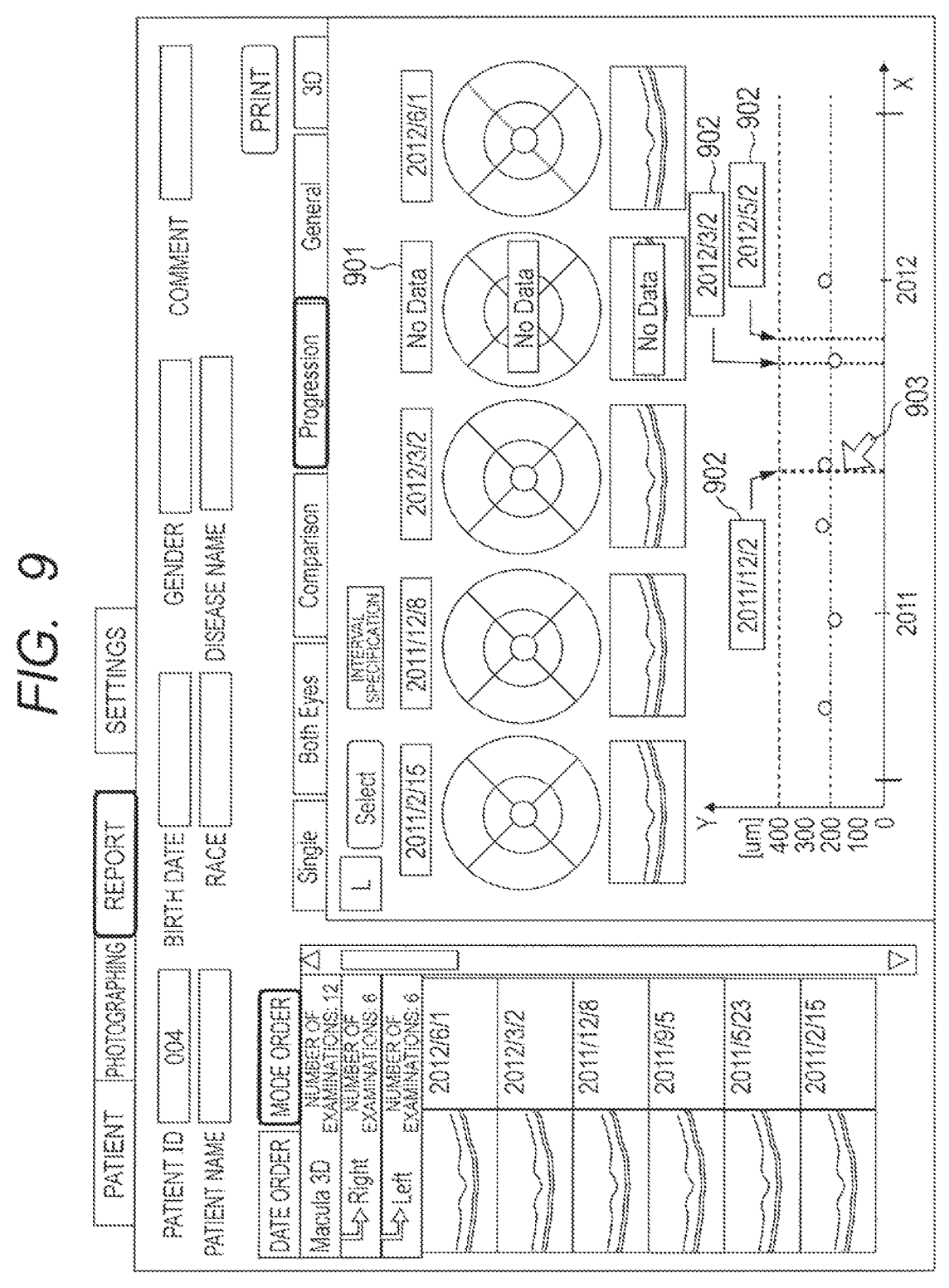

When the examination list in FIG. 4A is checked to confirm whether data exists within the range from 2012 May 17 to 2012 Apr. 1, it is found that no data exists. Hence, the individual interval date (1) 2012 May 2 is handled as an individual interval date for which there is no corresponding data. Since this individual interval date is excluded from the data extraction conditions, when determining the combinations, all combinations are determined for two examination data items because the number of data items is one fewer. Next, the differences with the individual interval dates (2) and (3) are calculated and totaled for the respective combinations, and the combination with the smallest total is determined. As a result, the combination shown in FIG. 4H is extracted. The extracted data is displayed as shown in FIG. 9. When there is no corresponding data, "No Data" 901 is displayed on the follow-up observation screen. On the graph, by displaying interval date displays 902 that include a marker and a date, the user can check intervals with respect to the entire period. Further, a configuration may also be adopted so that an interval date can be moved and adjusted by selecting one interval date display 902 with a mouse cursor 903 and dragging the selected interval date display 902 to the left or right.

Embodiment 4

Although in Embodiments 1 to 3 the entire range prior to the reference examination data is taken as a target for extraction of data, it is possible to extract and view data efficiently by specifying a target range of the follow-up observation. The following methods are conceivable as methods for specifying the range. Note that, as described above, data of the most recent examination is selected as the reference examination data. Also, since the remaining processing flow is the same as in Embodiments 1 to 3, a description thereof is omitted.

In the case of a method that sets a period to be taken as a predetermined period from the date of obtaining the reference examination data within which examination data is extracted, for example, a period of within two years is set. As another method, in a method that directly sets a predetermined date, for example, the predetermined date is set to 2011 Jun. 1 (though in practice, any appropriate date could be set). A further method is a method that allows the user to select the data to be taken as the oldest data from the examination list. When the user performs a right click operation after selecting the data of 2011 May 23 in the examination list shown on the "Select" screen in FIG. 8D, a menu 806 is displayed and the user can register the data by selecting "register as oldest data" 807. It is also possible to cancel a registration by selecting "cancel registration" 809 on the menu 806. A configuration may also be adopted that changes the display color of the registered data so that the user can distinguish the registered data from other data.

Embodiment 5

According to Embodiment 5, a method for registering data that the user wants to continually display and view or data that is key data when performing a follow-up observation is described. Note that since the remaining processing flow is the same as in Embodiments 1 to 4, a description thereof is omitted.

To register the aforementioned data, the user selects the data from the examination list. When the user performs a right click operation after selecting the data of 2011 May 23 in the examination list shown on the "Select" screen in FIG. 8D, the menu 806 is displayed and the user can register the data by selecting "register as continually displayed data" 808. It is also possible to cancel a registration by selecting "cancel registration" 809 on the menu 806. A configuration may also be adopted that changes the display color of registered data so that the user can distinguish the registered data from other data.

A method for displaying data registered as continually displayed data and extracted data in a mixed manner will now be described. First, as described in the foregoing, examination data is extracted in accordance with a predetermined extraction condition. After the data is extracted, continually displayed data and extracted data are combined and arranged in chronological order (or reverse chronological order) and displayed. If the number of data items exceeds the number of items that can be displayed, extracted data having the examination date that is nearest to the examination date of the continually displayed data is excluded, and the examination data is displayed by replacing the extracted data in question with the continually displayed data. It is thereby possible to perform a follow-up observation with respect to data that extends over a long period while viewing key data.

Other Embodiments

The present invention can also be realized by supplying software (a program) for realizing the functions of the above embodiments to a system or an apparatus via a network or via various storage media, and having a computer (or a central processing unit (CPU) or a micro processing unit (MPU)) of the system or apparatus read and execute the program.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

What is claimed is:

1. An information processing apparatus, comprising:
a hardware processor; and
a memory having instructions stored thereon which, when executed by the hardware processor, cause the information processing apparatus to:
select, in accordance with a user instruction, a plurality of two-dimensional images included in a specific period of time sequence data of a plurality of examination data obtained by analyzing a plurality of tomographic images of an eye obtained by optical coherence tomography at different examination dates, the plurality of examination data including retinal layer thicknesses of the eye; and
control a display device to (a) display the time sequence data in a first display area, to (b) display the selected plurality of two-dimensional images side by side in a second display area, the second display area being different from the first display area and to (c) display a two-dimensional image corresponding to a reference examination data selected from the plurality of examination data, in the second display area.

2. The apparatus according to claim 1, wherein the instructions, when executed by the hardware processor, further cause the display device to display the selected plurality of two-dimensional images arranged in a time sequence and side by side in a cross direction of the second display area, the first display area and the second display area being arranged side by side in a longitudinal direction of a display screen of the display device.

3. The apparatus according to claim 1, wherein the instructions, when executed by the hardware processor, further cause the display device to display the selected plurality of two-dimensional images and the time sequence data, arranged up and down.

4. The apparatus according to claim 2, wherein the instructions, when executed by the hardware processor, further cause the display device to display the selected plurality of two-dimensional images and the time sequence data, arranged up and down.

5. The apparatus according to claim 1, wherein the plurality of two-dimensional images each comprises an image representing a fundus layer thickness map or a fundus tomogram.

6. The apparatus according to claim 2, wherein the plurality of two-dimensional images each represents a fundus layer thickness map or a fundus tomogram.

7. The apparatus according to claim 3, wherein the plurality of two-dimensional images each represents a fundus layer thickness map or a fundus tomogram.

8. An information processing apparatus, comprising:
a hardware processor; and
a memory having instructions stored thereon which, when executed by the hardware processor, cause the information processing apparatus to:
obtain time sequence data of a plurality of examination data obtained by analyzing a plurality of tomographic images of an eye obtained by optical coherence tomography at different examination dates, and a plurality of two-dimensional images of the eye obtained at different examination dates, the plurality of examination data including retinal layer thicknesses of the eye; and
control a display device to (a) display the time sequence data in a first display area, to (b) display the obtained plurality of two-dimensional images in a second display area, the first display area and the second display area being arranged up and down, and to (c) display a two-dimensional image corresponding to a reference examination data selected from the plurality of examination data, in the second display area.

9. The apparatus according to claim 1, wherein the time sequence data is related to a fundus layer thickness.

10. The apparatus according to claim 2, wherein the time sequence data is related to a fundus layer thickness.

11. The apparatus according to claim 3, wherein the time sequence data is related to a fundus layer thickness.

12. The apparatus according to claim 1, wherein the time sequence data is an analysis image including an analysis map.

13. The apparatus according to claim 8, wherein the time sequence data is an analysis image including an analysis map.

14. The apparatus according to claim 1, wherein the time sequence data is a time sequence graph obtained by plotting a plurality of points corresponding to the plurality of examination data in time sequential order.

15. The apparatus according to claim 8, wherein the time sequence data is a time sequence graph obtained by plotting a plurality of points corresponding to the plurality of examination data in time sequential order.

16. The apparatus according to claim 8, wherein the time sequence data is related to a fundus layer thickness.

17. The apparatus according to claim 1, wherein the instructions, when executed by the hardware processor, further cause the plurality of two-dimensional images to be selected in accordance with a user operation to the time sequence data.

18. The apparatus according to claim 14, wherein the instructions, when executed by the hardware processor, further cause the plurality of two-dimensional images to be selected in accordance with a user operation to the time sequence graph.

19. The apparatus according to claim 8, wherein the instructions, when executed by the hardware processor, further cause the plurality of two-dimensional images to be selected in accordance with a user operation to the time sequence data.

20. The apparatus according to claim 8, wherein the plurality of two-dimensional images each represents a fundus layer thickness map or a fundus tomogram.

21. The apparatus according to claim 8, wherein the instructions, when executed by the hardware processor, further cause the display device to display the obtained plurality of two-dimensional images side in a cross direction of a display screen of the display device.

22. The apparatus according to claim 1, wherein the plurality of two-dimensional images are selected among two-dimensional images corresponding to the plurality of tomographic images.

23. The apparatus according to claim 1, wherein the plurality of two-dimensional images displayed side by side in the second display area are changed in accordance with the user instruction.

24. The apparatus according to claim 1, wherein the instructions, when executed by the hardware processor, further cause the display device to display a selection button for selecting the plurality of two-dimensional images, and further cause the display device to display a selection screen based on the user instruction executed on the selection button displayed by the display device, and
    wherein the plurality of two-dimensional images are selected by using the selection screen displayed by the display device.

25. The apparatus according to claim 8, wherein the plurality of two-dimensional images displayed side by side in the second display area are changed in accordance with a user instruction.

26. The apparatus according to claim 8, wherein the instructions, when executed by the hardware processor, further cause the display device to display a selection button for selecting the plurality of two-dimensional images, and further cause the display device to display a selection screen based on a user instruction executed on the selection button displayed by the display device,
    wherein the plurality of two-dimensional images are selected by using the selection screen displayed by the display device.

27. An information processing method comprising:
    selecting, in accordance with a user instruction, a plurality of two-dimensional images included in a specific period of time sequence data of a plurality of examination data obtained by analyzing a plurality of tomographic images of an eye obtained by optical coherence tomography at different examination dates, the plurality of examination data including retinal layer thicknesses of the eye; and
    controlling a display device to (a) display the time sequence data in a first display area, to (b) display the selected plurality of two-dimensional images side by side in a second display area, the second display area being different from the first display area, and to (c) display a two-dimensional image corresponding to a reference examination data selected from the plurality of examination data, in the second display area.

28. A non-transitory computer-readable storage medium storing a program for causing a computer to execute the method according to claim 27.

29. An information processing method comprising:
    obtaining time sequence data of a plurality of examination data obtained by analyzing a plurality of tomographic images of an eye obtained by optical coherence tomography at different examination dates, and a plurality of two-dimensional images of the eye obtained at different examination dates, the plurality of examination data including retinal layer thicknesses of the eye; and
    controlling a display device to (a) display the time sequence data in a first display area, to (b) display the plurality of two-dimensional images in a second display area, the first display area and the second display area being arranged up and down, and to (c) display a two-dimensional image corresponding to a reference examination data selected from the plurality of examination data, in the second display area.

30. A non-transitory computer-readable storage medium storing a program for causing a computer to execute the method according to claim 29.

31. The apparatus according to claim 1, wherein a two-dimensional image continually displayed on the display device is selected based on the user instruction, and
    wherein the instructions, when executed by the hardware processor, further cause the information processing apparatus to select another two-dimensional image different from the two-dimensional image continually displayed and cause the display device to display the selected another two-dimensional image.

32. The apparatus according to claim 8, wherein a two-dimensional image continually displayed on the display device is selected based on a user instruction, and
    wherein the instructions, when executed by the hardware processor, further cause the information processing apparatus to select another two-dimensional image different from the two-dimensional image continually displayed and cause the display device to display the selected another two-dimensional image.

33. The apparatus according to claim 1, wherein the plurality of two-dimensional images are displayed in a form of time by sequentially arranging the plurality of two-dimensional images from side to side on the second display area, and the time sequence data is displayed on the first display are located under the second display area.

34. The apparatus according to claim 1, executing a display control of:
    wherein the instructions, when executed by the hardware processor, further cause the display to change a display state from at least one of the displayed plurality of two-dimensional images to a two-dimensional image corresponding to examination data obtained at different examination date, in accordance with a user instruction through a displayed slide bar.

35. The apparatus according to claim 8, wherein the plurality of two-dimensional images are displayed in a form of time by sequentially arranging the plurality of two-dimensional images from side to side on the second display area, and the time sequence data is displayed on the first display are located under the second display area.

36. The apparatus according to claim 8,
    wherein the instructions, when executed by the hardware processor, further cause the display device to change a display state from at least one of the displayed plurality of two-dimensional images to a two-dimensional image corresponding to examination data obtained at different examination date, in accordance with a user instruction through a displayed slide bar.

37. The apparatus according to claim 1, wherein the instructions, when executed by the hardware processor, further cause the display device to display a two-dimensional image corresponding to the reference examination data at an end of horizontal direction of a display screen of the display device.

38. The apparatus according to claim 8, wherein the instructions, when executed by the hardware processor, further cause the display device to display a two-dimensional image corresponding to the reference examination data at an end of horizontal direction of a display screen of the display device.

39. The apparatus according to claim 1, wherein the instructions, when executed by the hardware processor, further cause the display device to change at least one of the plurality of two-dimensional images which are displayed, by a two-dimensional image corresponding to the examination data obtained on different examination date, in accordance with a user instruction.

40. The apparatus according to claim 8, wherein the instructions, when executed by the hardware processor, further cause the display device to change at least one of the plurality of two-dimensional images which are displayed, by a two-dimensional image corresponding to the examination data obtained on different examination date, in accordance with a user instruction.

41. The apparatus according to claim 1, wherein a data including the plurality of two-dimensional images which are displayed is output with a report format, in accordance with a user instruction.

42. The apparatus according to claim 8, wherein a data including the plurality of two-dimensional images which are displayed is output with a report format, in accordance with a user instruction.

43. The apparatus according to claim 1, wherein a predetermined number of examination data are extracted from the plurality of examination data by a predetermined extracting condition, for causing the display device to display the examination data, and
 the instructions, when executed by the hardware processor, further cause the display device to display a graph that plots in time sequential order a plurality of points corresponding to the plurality of examination data including the predetermined number of examination data, as a time sequential data.

44. The apparatus according to claim 8, wherein a predetermined number of examination data are extracted from the plurality of examination data by a predetermined extracting condition, for causing the display device to display the examination data, and
 the instructions, when executed by the hardware processor, further cause the display device to display a graph that plots in time sequential order a plurality of points corresponding to the plurality of examination data including the predetermined number of examination data, as a time sequential data.

\* \* \* \* \*